United States Patent [19]

Schroeder

[11] 4,109,156

[45] Aug. 22, 1978

[54] COLLIMATING DEVICE FOR X-RAYS

[76] Inventor: Charles H. Schroeder, P. O. Box 9414, Raytown, Mo. 64133

[21] Appl. No.: 765,969

[22] Filed: Feb. 7, 1977

[51] Int. Cl.² .............................................. G21K 1/00
[52] U.S. Cl. ..................................... 250/505; 250/479
[58] Field of Search ................................ 250/505, 479

[56] References Cited

U.S. PATENT DOCUMENTS

| 3,102,957 | 9/1963 | Slauson | 250/505 |
| 3,745,344 | 7/1973 | Updegrave | 250/479 |
| 3,864,576 | 2/1975 | Stevenson | 250/505 |

Primary Examiner—Alfred E. Smith
Assistant Examiner—T. N. Grigsby
Attorney, Agent, or Firm—Lowe, Kokjer, Kircher, Wharton & Bowman

[57] ABSTRACT

A position indicating device which attaches to an X-ray machine is provided with a collar onto which a lead lined cylinder may be threaded. The cylinder has an end plate through which a rectangular opening is formed in order to provide a rectangular X-ray beam for use in cephalometric radiography. When the cylinder is removed, a circular beam is emitted for use in intra-oral radiography.

10 Claims, 3 Drawing Figures

U.S. Patent  Aug. 22, 1978  4,109,156
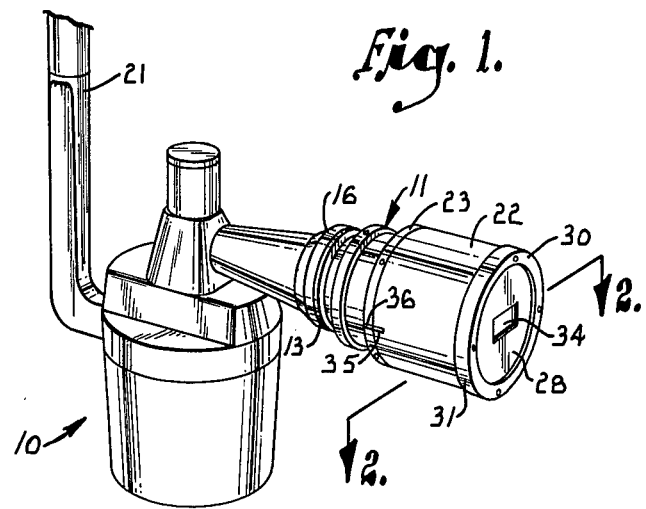
Fig. 1.
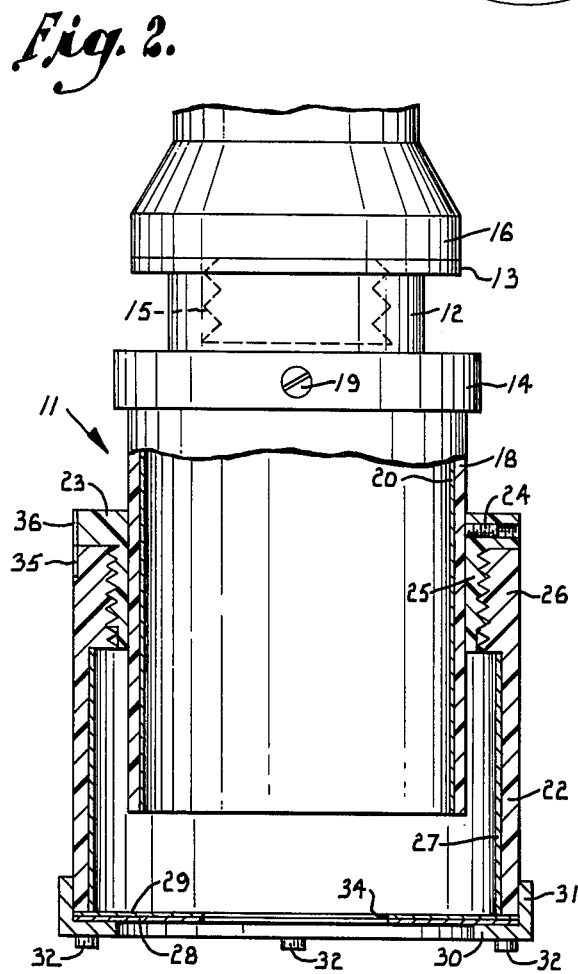
Fig. 2.
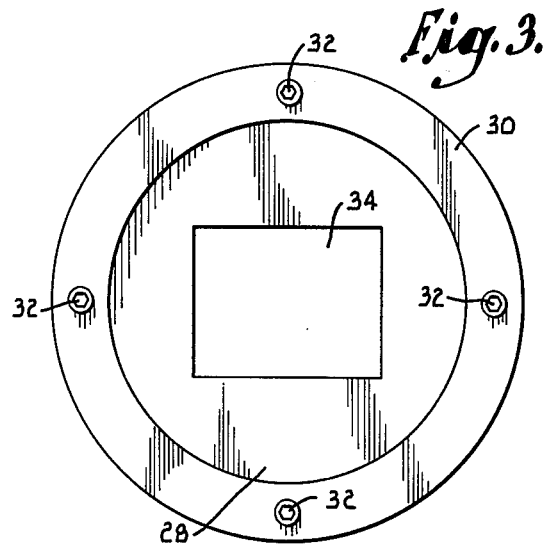
Fig. 3.
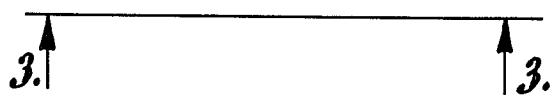

COLLIMATING DEVICE FOR X-RAYS

BACKGROUND AND SUMMARY OF THE INVENTION

This invention relates in general to dental radiography and more specifically to a collimating device which finds particular utility in cephalometric radiography.

In dental radiography, it is common for the patient to be given both intra-oral and cephalometric (extra-oral) X-rays. In the intra-oral process, the X-ray sensitive film is located within the mouth, while it is held in position behind the head in the extra-oral process. It has been the usual practice in the past to employ a single device known as a position indicating device (PID) or "cone" for both the intra-oral and extra-oral processes. The PID is essentially a lead lined cylindrical tube which attaches to the X-ray generator. The X-rays pass through a lead diaphragm in the PID and are thereby formed into a circular beam which is directed toward the patient and the X-ray sensitive film.

While the PID continues to be widely used for intra-oral X-rays, recent governmental regulations and general safety considerations have made it necessary to discontinue its use in the extra-oral process. These regulations require that the beam used in the taking of cephalometric X-rays conform in size and shape with the rectangular cassettes in which the X-ray film is contained. The present invention is directed to a collimating device which attaches to the PID in order to adapt it for use with the rectangular cassettes that are used in cephalometric radiography.

There have been attempts made to provide box-type attachments for the PID in order to form a rectangular beam. However, the devices that have been developed have not been entirely satisfactory, primarily because of their cost and complexity, and also because of the difficulty involved in attaching them to and removing them from the PID. Moreover, these devices often provide a beam which is either too large or too small when it reaches the patient and cassette. Each time the collimating device is attached to the PID, its rectangular aperture must be located exactly the same distance from the X-ray generator in order to provide a beam which is of the proper size when it reaches the patient, who is located a standard distance (60 inches) from the X-ray machine. However, existing collimators of this type are unable to be located with the required precision each time they are attached to the PID, and consequently they do not always collimate the beam accurately enough and with sufficient repeatability to satisfy government regulations or to conform with general safety standards.

It is an important object of the present invention to provide a collimating device which is able to be quickly and easily attached to a PID and which functions to produce a rectangular X-ray beam that conforms accurately in size, shape, and orientation with a standard film cassette of the type used in cephalometric radiography.

Another important object of the invention is to provide a collimating device in which the rectangular opening that collimates the beam is located at exactly the same distance from the X-ray generator and in the same rotative position each time the device is attached to the PID. This is a significant feature of the invention because it assures that the beam will always coincide precisely with the cassette in size and shape.

Yet another object of the invention is to provide a collimating device of the character described which may be used with existing X-ray generators of various types.

A further object of the invention is to provide a collimating device of the character described which effectively shields against X-ray leakage.

An additional object of the invention is to provide a collimating device of the character described which is constructed simply and economically and which operates safely.

Other and further objects of the invention, together with the features of novelty appurtenant thereto, will appear in the course of the following description.

DETAILED DESCRIPTION OF THE INVENTION

In the accompanying drawing which forms a part of the specification and is to be read in conjunction therewith and in which like reference numerals are used to indicate like parts in the various views:

FIG. 1 is a perspective view illustrating the collimating device of the present invention attached to a conventional X-ray machine;

FIG. 2 is an enlarged fragmentary view taken partially in cross-section generally along line 2—2 of FIG. 1 in the direction of the arrows; and FIG. 3 is an end elevational view taken generally along line 3—3 of FIG. 2 in the direction of the arrows.

Referring now to the drawing in detail and initially to FIG. 1, reference numeral 10 generally designates a conventional X-ray machine or tubehead from which X-rays are emitted. The X-ray machine may be of any suitable type. The construction and manner of operation of such machines are well known to those having skill in the art and need not be described in detail herein.

Numeral 11 generally designates a device which is known in the trade as a "cone" or position indicating device (PID). With reference to FIG. 2, the PID 11 is in the shape of a tube and includes a sleeve portion 12 which carries a flange 13 at one end and an enlarged ring 14 at the opposite end. The sleeve 12 is internally threaded in order to connect with threaded shaft 15. The shaft 15 projects from an enlarged end portion 16 of the X-ray head 10 and is hollow in order to receive the X-rays which are emitted therefrom. Flange 13 fits closely against portion 16 when the PID is fully threaded onto shaft 15.

The tube portion 18 of the PID is fit in and secured to ring 14 by screws 19. Tube 18 is co-axial with shaft 15 and is able to receive the X-rays that pass through the shaft. The tube may be constructed of hard plastic or any other suitable material, and it has a lead lining 20 secured to its cylindrical inner wall surface to prevent X-rays from passing through the tube walls. The circular outer end of tube 18 is open in order to form the X-rays into a circular beam which may be used in intra-oral radiography.

As thus far described, the PID 11 is conventional, and its normal use is in intra-oral radiography. An adjustable mounting arm 21 (FIG. 1) on which the X-ray head 10 is carried allows the PID to be placed with its open end against the facial area of the patient. The X-rays pass through shaft 15 and into tube 18 where they are formed into a circular beam which passes out of the open end of the tube. The beam is directed toward the teeth of the patient and onto X-ray sensitive film which is located within the mouth behind the teeth.

In accordance with the present invention, a collimating device in the form of a cylinder 22 is provided. A circular collar 23 is secured to tube 18 in order to provide an attachment by which the cylinder 22 may be mounted on the PID. The collar fits closely around tube 18 and is locked thereto by set screws 24. Collar 23 is preferably located intermediate of the ends of tube 18 near the center thereof. A sleeve 25 extends integrally from collar 23 and closely around the outside wall of tube 18. Sleeve 25 is externally threaded in order to mate with internal threads which are formed on a thickened end portion 26 of cylinder 22. When the cylinder is threaded onto sleeve 25, it is co-axial with tube 18 and surrounds the open end thereof. The inner wall surface of cylinder 22 is provided with a lead lining 27 which terminates at portion 26.

Cylinder 22 is provided with a thin end plate 28 which has a lead lining 29 secured to its inside surface. The end plate 28 is secured over the outer end of the cylinder by a circular metal rim 30 which fits against the peripheral portion of the plate. The rim 30 has an integral flange 31 which fits closely around the outside surface of cylinder 22 at the outer end portion thereof. Screws 32 attach rim 30 and plate 28 to the cylinder.

As best shown in FIG. 3, a rectangular opening 34 is formed substantially centrally through plate 28 and its lining 29. Opening 34 is somewhat smaller than the circular open end of tube 18 and is spaced outwardly thereof.

To assist in properly locating cylinder 22, a pair of alignment marks 35 and 36 (FIGS. 1 and 2) are provided on the cylinder and on collar 23, respectively. The marks 35 and 36 are located such that when cylinder 22 is tightened down on sleeve 25 and the marks are aligned with one another, opening 34 will be spaced properly from the X-ray generator to provide a beam having the desired size when it reaches the patient.

When cylinder 22 is removed from collar 23, the PID 11 can function in the manner previously described to assist in intra-oral radiography. The cylinder is installed on the tubehead when extra-oral or cephalometric radiography is to be carried out. The X-rays which enter cylinder 22 from the end of tube 18 encounter the rectangular opening 34 which forms them into a rectangular beam that is directed toward the head of the patient and onto an X-ray film cassette which is located behind the patient. The sleeve 12 provides a recessed area between flange 13 and ring 14 that is suitable to receive a clamp or other suitable means (not shown) which is used to secure the X-ray head in a stationary position during the cephalometric process. The clamp or other device may alternatively attach in the area of tube 18 located between ring 14 and collar 23.

It is standard practice for the center of the patient's head to be located exactly 60 inches from the X-ray machine, and for the rectangular film cassette to be held directly behind the head of the patient. Accordingly, each time the collimating device is installed on the PID, the opening 34 must be positioned exactly the same distance from the X-ray machine if the beam is to coincide with the cassette. Since collar 23 is fixed on the PID 11 and the PID is fixed on the X-ray machine, tightening of cylinder 22 to the same extent each time it is threaded onto the collar will result in the end plate 28 always being the same distance from the end of tube 18 (and thus the same distance from the X-ray machine). The alignment marks 35 and 36 are located such that when the cylinder is tightened sufficiently for the marks to align with one another, opening 34 will be so located to provide a beam that is 8 inches high and 10 inches wide at 60 inches from the machine, thereby conforming with the film in the cassette. Of course, beams having other sizes can be obtained by utilizing an opening larger or smaller than opening 34. Also, adjustment of the size of the beam may be achieved by moving collar 23 toward or away from the outer end of PID 11. Moving toward the end reduces the beam size at the cassette, while moving away increases the beam size at the cassette. In addition, alignment of the marks assures that opening 34 is in the same rotative orientation as the cassette (see FIG. 3).

When cylinder 22 is fully tightened onto sleeve 25, the thickened end portion 26 abuts collar 23. Therefore, the alignment marks 35 and 36 are not always necessary because the cylinder can often be tightened in relatively accurate fashion by feel alone. However, the alignment marks are preferably employed because they assure accuracy even if the threads become worn or otherwise damaged.

It is thus apparent that the PID 11 may be used alone for intra-oral radiography and with cylinder 22 for extra-oral radiography, and that conversion between the two uses may be carried out quickly and easily. The provision of a threaded connection between the collimating cylinder 22 and the PID 11 facilitates the installation and removal of the cylinder, and it is therefore preferred over other types of connections. Also, the threaded connection permits the cylinder to be tightened to the same extent each time it is installed, and the accuracy and repeatability of the collimating device is therefore enhanced.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative and not in a limiting sense.

Having thus described the invention, I claim:

1. A collimating device for use with a substantially tubular member which is attachable to an X-ray generator and which has an open end for providing an X-ray beam that may be used in intra-oral radiography, said collimating device comprising:
   a substantially hollow member large enough to fit around the open end of said tubular member and having walls which are impervious to X-rays;
   an end portion of said hollow member presenting a substantially rectangular opening through which X-rays may pass in a beam of substantially rectangular shape; and
   means for detachably mounting said hollow member on the tubular member with said walls surrounding the open end thereof and with said rectangular opening spaced a preselected distance from said open end.

2. The collimating device of claim 1, including means indicating when said rectangular opening is located at said preselected distance from said open end of the tubular member.

3. The collimating device of claim 1, wherein said detachable mounting means comprises:
   a collar adapted to fit around said tubular member;
   means for securing said collar to the tubular member; and
   means establishing a detachable connection between said collar and hollow member to mount the latter on said tubular member.

4. The collimating device of claim 3, wherein said connection is a threaded connection of said hollow member with said collar.

5. The collimating device of claim 4, including a first mark on said collar and a second mark on said hollow member, said second mark being alignable with said first mark to indicate when said hollow member is threaded onto said collar to the extent necessary to locate said rectangular opening at said preselected distance from the open end of said tubular member.

6. Collimating apparatus for use with an X-ray generator, said apparatus comprising in combination:
   a generally cylindrical tube adapted for attachment to the X-ray generator to receive the X-rays emitted therefrom, said tube having walls which are impervious to X-rays and a generally circular open end for providing an X-ray beam which may be used in intra-oral radiography;
   a collimator having walls which are impervious to X-rays and which are large enough to surround the open end of said tube;
   an end of said collimator presenting a substantially rectangular opening through which the X-rays pass in a substantially rectangular beam which may be used in extra-oral radiography; and
   means for detachably mounting said collimator on said tube with the collimator walls surounding the open end of said tube and with the rectangular opening of said collimator located a preselected distance from the open end of said tube.

7. The apparatus set forth in claim 6, including means indicating when said rectangular opening is located said preselected distance from the open end of said tube.

8. The apparatus set forth in claim 6, wherein said detachable mounting means comprises:
   a collar extending around and secured to the walls of said tube; and
   means establishing a detachable connection between said collar and collimator to mount the latter to said tube.

9. The apparatus of claim 8, wherein said connection is a threaded connection of said collimator with said collar.

10. The apparatus of claim 9, including a mark on said collar and a mark on said collimator which is alignable with the mark on said collar to indicate when said cylinder is threaded onto said collar to the extent required to locate said rectangular opening at said preselected distance from the open end of said tube.

* * * * *